United States Patent [19]
Barath

[11] Patent Number: 5,616,149
[45] Date of Patent: Apr. 1, 1997

[54] BALLOON CATHETER WITH CUTTING EDGE

[75] Inventor: Peter Barath, W. Hollywood, Calif.

[73] Assignee: Cedars-Sinai Medical Center, Los Angeles, Calif.

[21] Appl. No.: 219,997

[22] Filed: Mar. 28, 1994

Related U.S. Application Data

[62] Division of Ser. No. 757,847, Sep. 11, 1991, abandoned, which is a division of Ser. No. 547,957, Jul. 3, 1990, Pat. No. 5,196,024.

[51] Int. Cl.$^6$ .......................... A61B 17/32; A61M 25/10
[52] U.S. Cl. .......................... 606/159; 606/170; 606/191; 606/192; 606/194; 128/772; 604/96
[58] Field of Search .................. 604/96, 98, 264, 604/280; 606/159, 167, 170, 191, 192, 194; 128/772

[56] References Cited

U.S. PATENT DOCUMENTS

| | | | |
|---|---|---|---|
| 4,574,781 | 3/1986 | Chin | 606/167 |
| 4,799,479 | 1/1989 | Spears | 606/28 X |
| 4,886,061 | 12/1989 | Fischell et al. | 606/159 |
| 4,921,483 | 5/1990 | Wijay et al. | 604/96 |
| 4,921,484 | 5/1990 | Hillstead | 606/159 |
| 4,966,604 | 10/1990 | Reiss | 606/159 |
| 5,009,659 | 4/1991 | Hamlin et al. | 606/159 |
| 5,049,131 | 9/1991 | Deuss | 604/96 |
| 5,087,246 | 2/1992 | Smith | 604/96 |
| 5,100,424 | 3/1992 | Jang et al. | 606/159 |
| 5,116,318 | 5/1992 | Hillstead | 606/192 |
| 5,156,610 | 10/1992 | Reger | 606/159 |
| 5,196,024 | 3/1993 | Barath | 606/159 |
| 5,209,749 | 5/1993 | Buelna | 606/159 |
| 5,320,634 | 6/1994 | Vigil et al. | 606/159 |

FOREIGN PATENT DOCUMENTS

| | | | |
|---|---|---|---|
| 2804015 | 8/1979 | Germany | 606/159 |
| 3326648 | 7/1985 | Germany . | |
| 3402573 | 8/1985 | Germany . | |
| 3519626 | 12/1986 | Germany | 606/159 |
| 3607295 | 9/1987 | Germany | 606/159 |
| 3732236 | 12/1988 | Germany | 606/159 |
| 1516120 | 10/1989 | U.S.S.R. | 606/191 |
| 1547328 | 6/1979 | United Kingdom | 604/96 |

*Primary Examiner*—Krista M. Zele
*Attorney, Agent, or Firm*—Lyon & Lyon

[57] ABSTRACT

An apparatus and method for dilation or recanalization of a diseased vessel by use of a balloon catheter with cutting edges to make longitudinal cuts in the vessel wall is described. The diameter of the vessel is increased without the subsequent secondary cellular proliferation or restenosis in the vessel caused by conventional angioplasty methods.

2 Claims, 12 Drawing Sheets

BALLOON CATHETER WITH CUTTING EDGE

RELATED APPLICATION

This is a Divisional application of Ser. No. 07/757,847 filed Sep. 11, 1991, now abandoned, which is in turn a Divisional application of Ser. No. 07/547,957 filed Jul. 3, 1990, now U.S. Pat. No. 5,196,024.

This invention relates to a means and method for dilation or recanalization of a diseased vessel. More particularly, this invention relates to a balloon catheter with cutting edges and its use for making regular longitudinal surgical cuts in the vessel wall, thereby increasing the diameter of the vessel and decreasing or eliminating the subsequent secondary cellular proliferation or restenosis in the vessel wall caused by conventional angioplasty methods.

BACKGROUND

Atherosclerotic cardiovascular disease is a common cause of death in industrialized countries (AJR 150:1263–1269 (1988)), and is characterized by a narrowing of the arterial lining due to atherosclerotic plaques. Surgical methods of treating this disease, including bypass techniques, have resulted in significant medical advancement. A need exists however, for a treatment with less expensive and less invasive procedures.

Percutaneous transluminal angioplasty, or balloon angioplasty, of peripheral and coronary arteries has proven to be a useful nonsurgical procedure for the treatment of localized arterial lesions due to atherosclerosis, and has become a promising non-surgical alternative to bypass surgery. (*Merck Manual*, 15th Ed. p. 559). The technique consists of inserting an uninflated balloon-tipped catheter into the affected artery. Dilation of the diseased segment of artery is accomplished by inflating the balloon which pushes the atherosclerotic lesion outward, thereby enlarging the arterial diameter. Typically, inflation is repeated two additional times. The balloon is then deflated and the catheter is withdrawn.

Following balloon angioplasty, blood flow through the artery is usually significantly improved. The primary success rate of the technique is around 90–95%. Intimal flap, abrupt occlusion due to acute thrombus formation, dissection of the artery, elastic recoil of the vessel wall, and the inability to pass the stenotic area however, are mostly responsible for acute failure of the procedure. In addition, long term success is complicated by a high rate (35–40%) of late restenosis usually within 3 to 6 months. As a result, about one-third of all patients treated with balloon angioplasty return for a second or third procedure. (*Eur. Heart J.* 9:31–37 (1988)). A need exists therefore, for a method to decrease acute failure and increase the long-termbenefits of balloon angioplasty, with the aim of preventing restenosis of the diseased vessel.

The physiological basis of restenosis after balloon angioplasty is an accelerated, probably modified smooth muscle cell proliferation and secondary ground substance (collagen, etc.) deposition initiated by the angioplasty procedure itself. This accelerated proliferation of cells primarily results from the extensive traumatic damage to the vessel wall which occurs following conventional balloon dilation, partially due to the pressures (6–12 atm) applied to overcome the elastic recoil. The traumatic damage includes stretching of the media and adventitia. This leads in turn to growth factor expression in the smooth muscle and adventitial cells which stimulates cell proliferation and an "overshot" of the normal healing process, as in keloid formation. In addition, irregular intimal tears occur which expose the deeper highly thrombogenic layers of the vessel to the blood and provoke attachment of cellular elements such as platelets, neutrophils and monocytes, with deliberation of growth factors such as platelet derived growth factor (PDGF). (Walker et al., *Proc. Acad. Sci* 83:7311–7315 (1986)). Further, it has recently been suggested that the mechanism of balloon dilation primarily affects the normal vessel wall (vs. the diseased areas), inducing a higher proliferative response from the normal area. (Gravanis et al., *Human Pathol* 20:477–485 (1989)).

Other techniques to recanalize diseased vessels or make incisions in a vessel wall have been described, but those that remove the bulk of the atherosclerotic lesion actually provoke more extended injury in the vessel and result in a higher reparative/proliferative response than with balloon angioplasty. (Simpson et al., *Circ,* 90(4):2311A (1989)). Ginsburg et al., U.S. Pat. No. 4,790,310 combines laser and balloon angioplasty to reopen stenosed arteries; Bonnet, U.S. Pat. No. 4,712,547 describes an instrument for slitting stenosis in the ureter; Korth, et al., U.S. Pat. No. 4,633,860 relates to a device that creates incisions in the skin and tissue beneath the skin, forming a canal for inserting an endoscope for percutaneous nephroscopy; Lary, U.S. Pat. No. 4,273,128 describes a surgical instrument for coronary cutting and dilating a vessel or to "valve" a stenotic mass to facilitate smooth introduction of a balloon catheter to the center of the stenosis; Hoffman, U.S. Pat. No. 2,730,101 describes a cutter means usable in opening clogged milk ducts; Richter, U.S. Pat. No. 2,655,154 describes a valvulotome for operating on the pulmonary valve; Mallman, U.S. Pat. No. 518,600 describes an instrument for cutting urethral strictures; and USSR publication 938977 depicts a retractable blade extendable by pneumatic pressure. None of these devices and methods is intended for increasing the diameter of a vessel by producing regular longitudinal surgical cuts in the vessel wall, and decreasing or eliminating subsequent secondary cellular proliferation or restenosis. Many of these devices may actually provoke a higher reparative/proliferative response.

SUMMARY

The present invention provides a means and method for recanalizing and dilating a diseased vessel, and facilitating balloon angioplasty procedures, which avoids the cited disadvantages of current techniques. The invention provides a catheter system which makes a surgical incision within the vessel wall that is sharp and regular in terms of length, depth and direction. This regular cutting enhances the success of the angioplasty procedure by overcoming elastic recoil, cutting harder fibrotic and calcified atheromas and obtaining a more regulated and localized surgical wound which repairs without the overwhelming proliferation of the intimal cells.

Several designs of the angioplasty balloon catheter may be suitable for the present invention. A common characteristic of the cutting balloon is the presence of sharp cutting edges situated parallel with the longitudinal axis of the balloon. The height of the cutting edges may vary depending on the anatomical character of the vessel, with an aim to cut into but not entirely through the vessel wall. In a preferred embodiment, the cutting edges penetrate 70–80% of the vessel medial layer. The number of cutting edges may vary, be of different profiles, and made of different materials with an aim to induce sharp longitudinal cuts in the lumen surface of the vessel upon inflation of the balloon. In addition, the cutting edges may be articulated at various intervals to increase the flexibility of the device and enable the balloon catheter to negotiate the curvature of the vessels.

Although the embodiment described here relates to the use of the cutting balloon for dilation and recanalization of an artery affected by atherosclerotic plaque and/or thrombus, it is readily apparent that the invention may be used to dilate or recanalize any narrowed or obstructed vessel.

DETAILED DESCRIPTION OF THE INVENTION

As discussed above, several different designs of the cutting balloon catheter may be suitable for the present invention. The cutting edges may be of different profiles and made of various substances including metal or hard plastic, so long as the edge fabrication produces sharp longitudinal cuts in the luminal surface of the vessel upon inflation of the balloon. Although not intended to limit the present invention, five possible designs of a cutting balloon catheter are described below.

Figure 1:
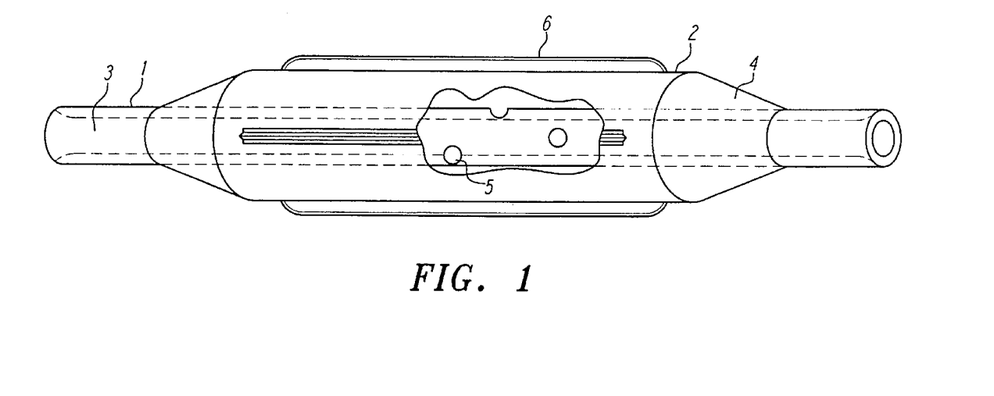
FIG. 1 is a side view illustrating the invention.

FIG. 1 shows a side view of one preferred embodiment of the cutting balloon catheter of the present invention, consisting of a catheter shaft (1), and a lumen with an inflatable balloon (2), in its inflated state, at the distal end. In the catheter shaft, there is a central lumen (3) and a coaxial lumen (4). The central lumen accommodates the catheter guide wire and provides a channel for injection of the contrast material. The coaxial lumen serves to inflate the balloon through side holes (5). Sharp longitudinal processes or cutting edges (6) protrude parallel with the longitudinal axis of the surface of the balloon. Periodic articulations may be incorporated into these cutting edges without interruption of the edge continuity. In this particular embodiment, the cutting edges are solid plastic protrusions formed at the time of balloon manufacture. The proximal end of the catheter is formed by two Luer connections, which may be coupled to a hemostatic side arm adapter and to an inflator device.

Figure 2:
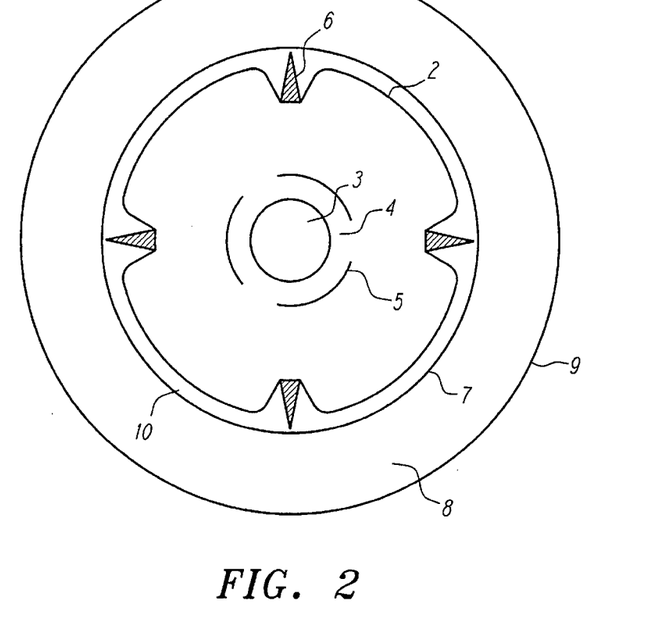
FIG. 2 is a cross-section view with the balloon of the invention in the deflated state.

FIG. 2 is a cross-section of the cutting balloon catheter of FIG. 1, positioned within a normal or concentrically diseased vessel wall (7, 8, 9). The balloon shown here is in a deflated state with the cutting edges (6) retracted and covered by the folds of the balloon (2).

Figure 3:
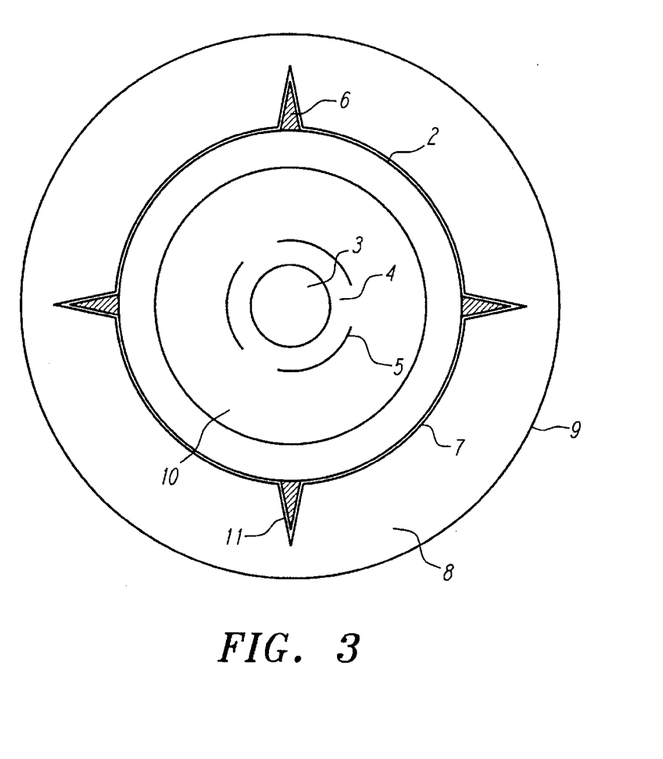
FIG. 3 is a cross-sectional view with the balloon of the invention in the inflated state.

FIG. 3 is another cross-section of the cutting balloon catheter of FIG. 1 positioned within a normal or concentrically diseased vessel. Here, the balloon is inflated (2) and the cutting edges (6) penetrate into the vessel wall (7, 8) making longitudinal cuts with sharp margins (11) in the vessel wall.

Figure 4:
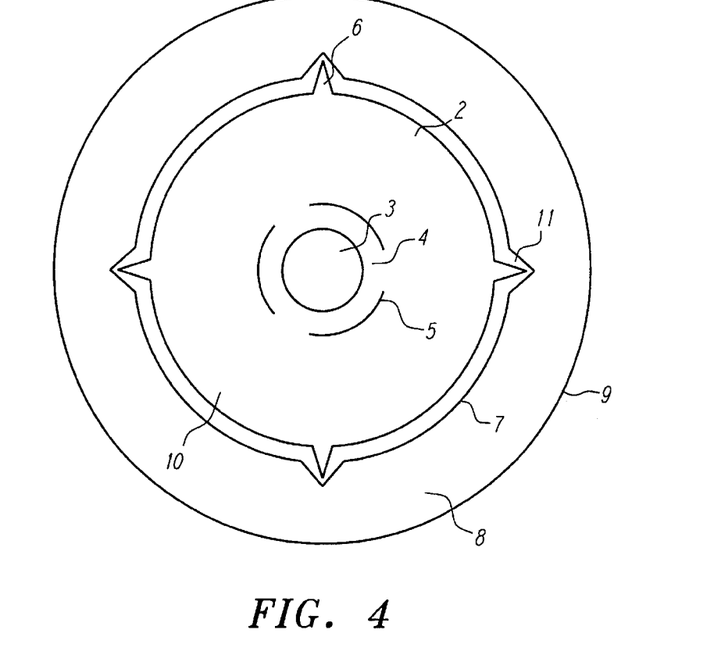
FIG. 4 is a cross-sectional view with the balloon of the invention further inflated.

FIG. 4 is the cutting balloon catheter of FIG. 3 when the working pressure (approximately 3–6 atm) of the balloon is built up by further inflation of the balloon. Here the diameter of the vessel is increased at the expense of pulling apart the margins of the cuts (11) without traumatic stretching of the remainder of the vessel wall.

Figure 5:
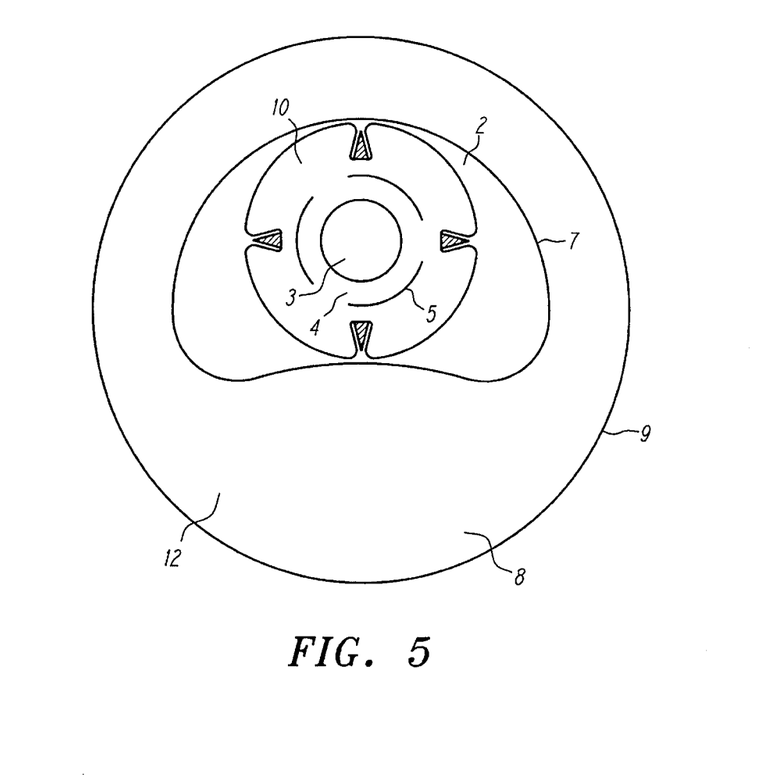
FIG. 5 is a cross-sectional view with the balloon of the invention in the deflated state.
Figure 6:
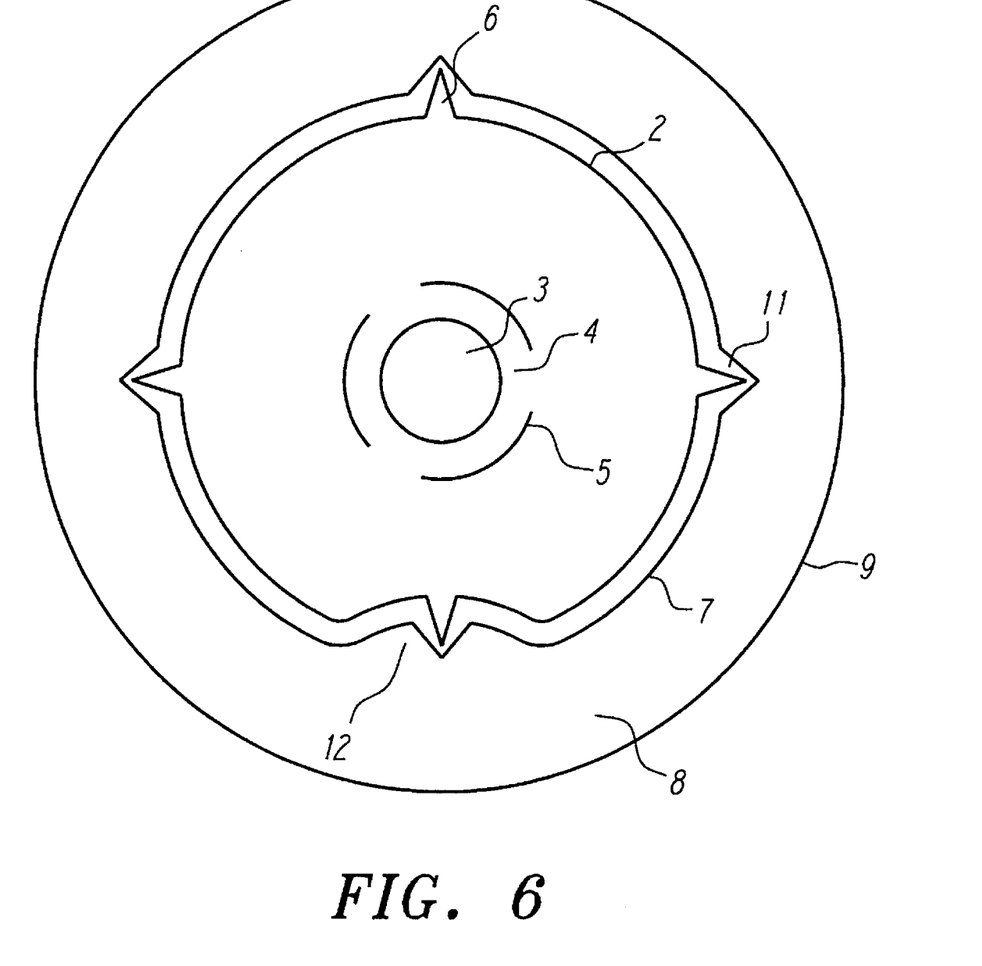
FIG. 6 is a cross-sectional view after inflation of the balloon of the invention.

FIG. 5 shows a cross-section of the deflated cutting balloon catheter of FIG. 1 within a vessel containing an eccentric atherosclerotic plaque (12). FIG. 6 shows the vessel depicted in FIG. 5 after inflation of the balloon (2). The cutting edges (6) penetrate into the vessel wall (7, 8) making cuts with sharp margins (11) and pulling the margins apart thereby increasing the vessel diameter.

In practice, the cutting balloon catheter shown in FIG. 1 is delivered to the area of intervention in deflated form (FIG. 2). In this embodiment, the balloon is folded up around the cutting edges to prevent injury of the vessel during delivery. Once the catheter is positioned within the vessel at the site of intervention, the balloon is inflated allowing the cutting edges to penetrate into the vessel lumen (FIG. 3). As inflation is completed and the working pressure (3–6 atm) within the balloon builds, the diameter of the diseased vessel increases as the cuts made by the balloon open (FIG. 4). It should be noted that the cutting (FIG. 3) and dilation (FIG. 4) phase are a continuum. A properly selected balloon diameter prevents overdilation and cutting too deep into the vessel wall.

Figure 7:
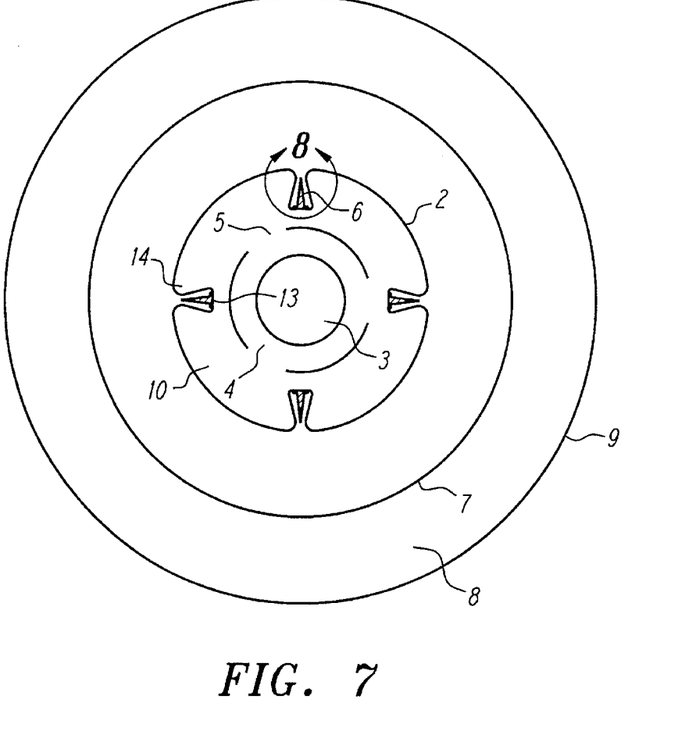
FIG. 7 is a cross-sectional view of the invention.
Figure 8:
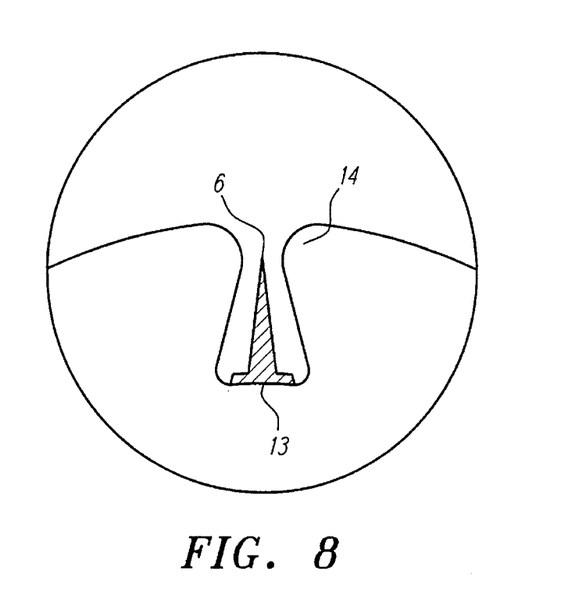
FIG. 8 is a partial cross-sectional view of the invention.

In a second embodiment of the invention, the balloon cutting edges are fabricated of metal. FIG. 7 and its cut-out FIG. 8 show a metallic cutting edge (6) which is sitting on a metallic plate (13). The metallic plate and edges are discrete sections, preferably 1–2 mm in length, and mounted onto the balloon surface in a row parallel with the longitudinal axis of the balloon, thereby providing articulation to the device. The edges are covered by folds (14) of the balloon in the deflated state.

Figure 9:
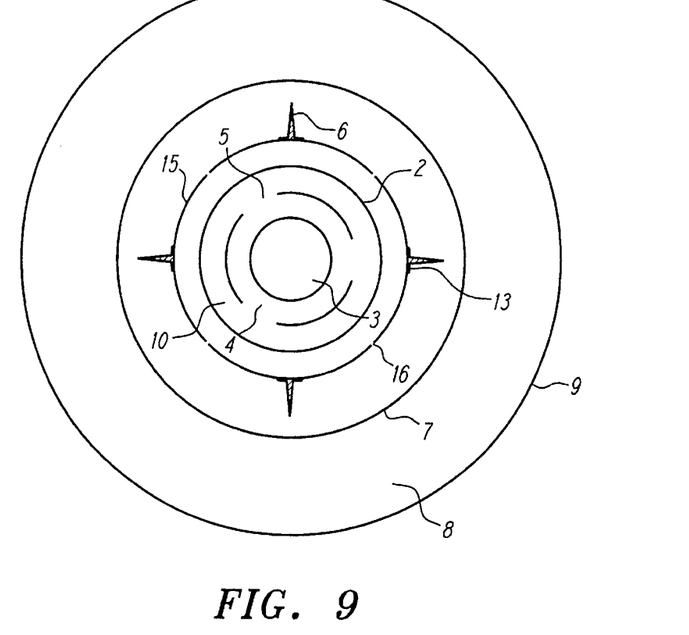
FIG. 9 is a cross-sectional view of the invention which includes a casing around the deflated balloon.

FIG. 9 shows a cross-section of a third embodiment of the invention within a vessel wall. Here, there is a plastic casing (15) around the balloon (2). Continuity of the casing surface is interrupted by longitudinal slots (16). The metallic cutting edges (6) with plates (13) similar to FIG. 8 are lined up on the solid section of the casing.

Figure 10:
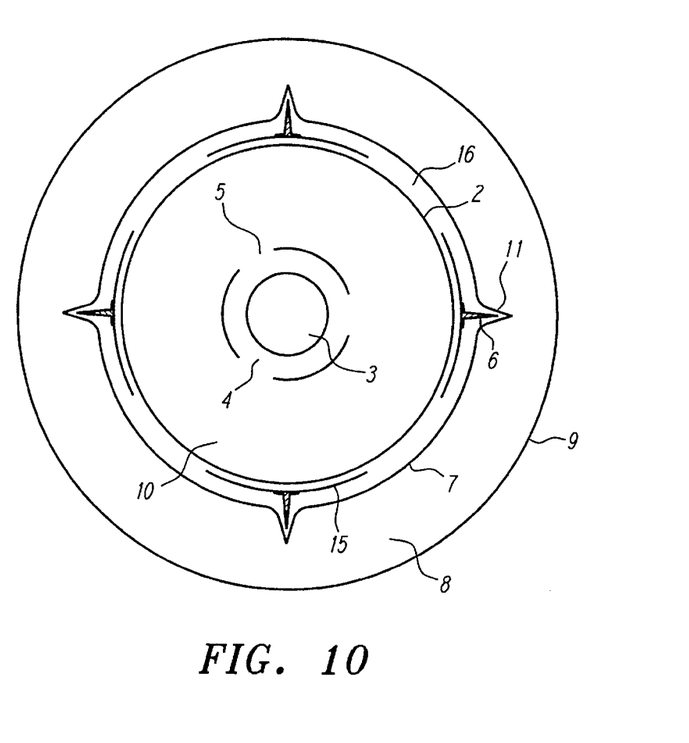
FIG. 10 is a cross-sectional view of the invention which includes a casing around the inflated balloon.

FIG. 10 shows the embodiment of FIG. 9 after the balloon has been inflated. Upon inflation of the balloon, the margins of the casing (15) move away from each other, increasing the size of the longitudinal slots (16) and exposing the surface of the balloon (2). At the same time, the cutting edges (6), penetrate into the vessel wall producing cuts with sharp margins (11).

Figure 11:
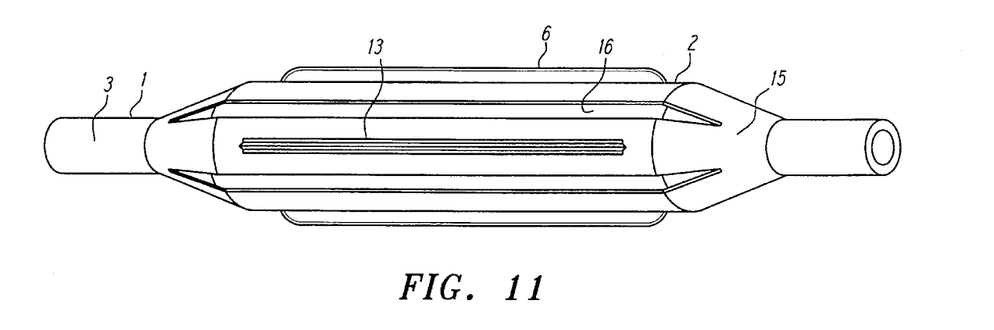
FIG. 11 is a longitudinal view of the invention.

FIG. 11 is a longitudinal view of the cutting balloon in FIG. 9 and 10 with the balloon in an inflated state. The cutting edges (6) sitting on metal plates (13) are mounted on the surface of the longitudinal sections of the plastic casing (15). The longitudinal slots (16) are pulled apart by inflation of the balloon, and expose the balloon surface (2).

Figure 12:
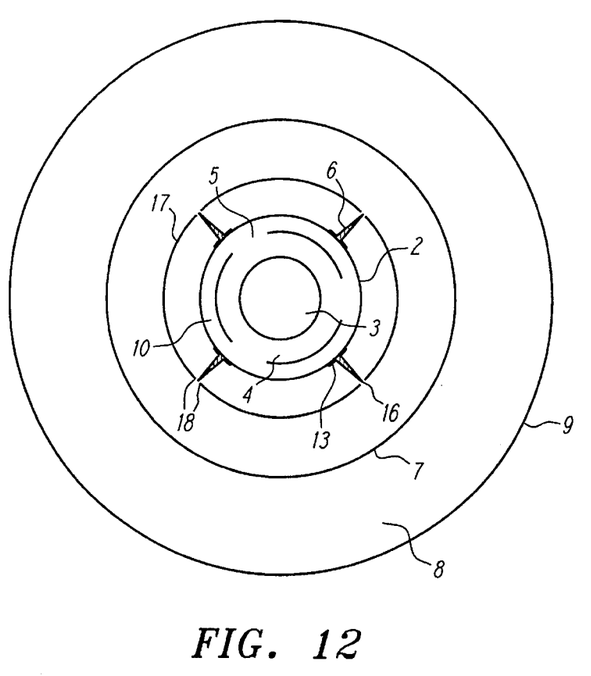
FIG. 12 is a cross-sectional view of the invention which includes a protective sheath about the deflated balloon.

FIG. 12 shows a cross-section of a fourth possible embodiment of the invention within a vessel wall. Here, a protective sheath (17) covers the entire balloon. The metallic cutting edges (6) with plates (13) (similar to embodiment in FIG. 8) are lined up on the longitudinal axis of the balloon (2). Continuity of the sheath is interrupted by longitudinal groves (18), which serve to accommodate, guide, and protect the tips of the cutting edges. The protective sheath prevents vessel injuries during delivery and holds the cutting edges in proper position prior to balloon inflation.

Figure 13:
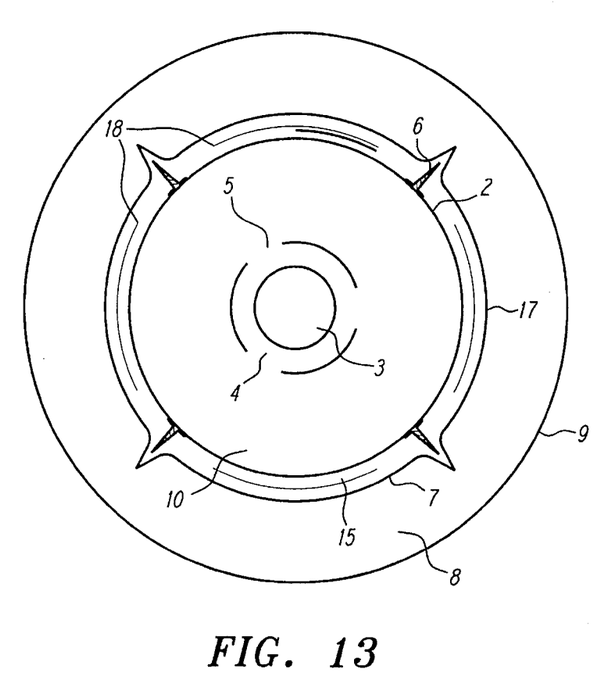
FIG. 13 is a cross-sectional view of the invention which includes a protective sheath about the inflated balloon.

FIG. 13 shows the embodiment of FIG. 12 with the balloon in the inflated state. The grooves (18) of the protective sheath (17) open up allowing the cutting edges (6) to penetrate into the vessel wall (7, 8) producing cuts with sharp margins (11). After deflation, the cutting edges retract behind the protective sheath thereby avoiding injury to the vessel during withdrawal of the cutting balloon.

Figure 14:
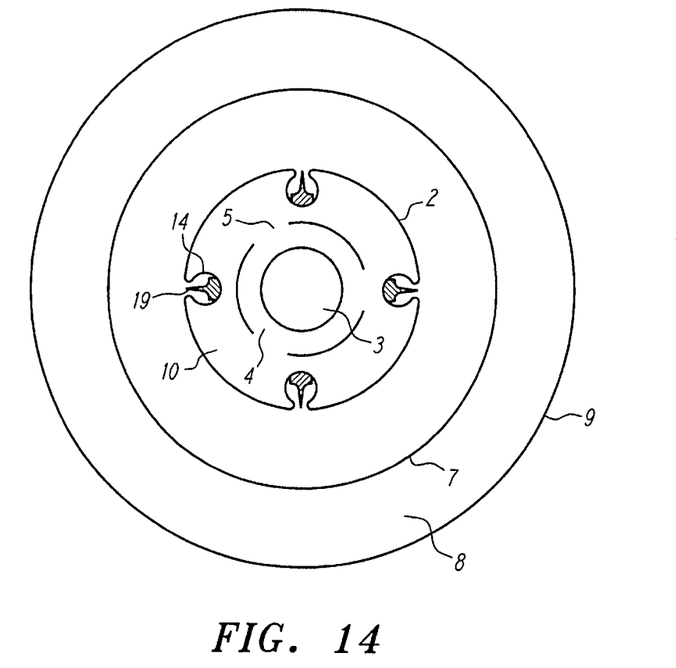
FIG. 14 is a cross-sectional view of the invention which includes shaped wires and the deflated balloon.

FIG. 14 shows a cross-section of a fifth embodiment of the invention in deflated state. In this embodiment the cutting edges (6) are formed of specially shaped wires sitting in grooves (19) on the balloon (2) surface. The wires are shaped in such way that their cross-section is similar to a hobnail i.e. a short nail with a thick head.

Figure 15:
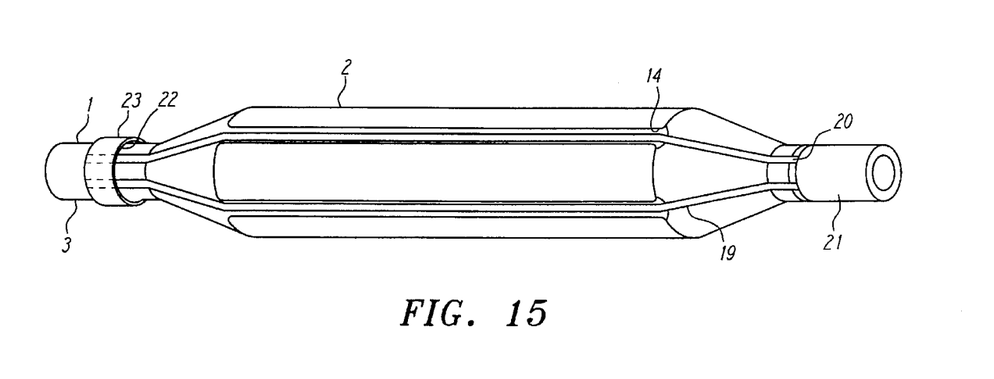
FIG. 15 is a longitudinal view of FIG. 14

FIG. 15 shows a longitudinal view of the device in FIG. 14. The distal ends (20) of the wires are fixed to the distal part of the catheter shaft (21) while the proximal end of the wire (22) goes underneath a ring (23) placed around the catheter shaft (1). The wires can freely slide under the ring. The wires are not mounted in other places to the balloon surface allowing a free sliding longitudinal motion of the wires along the longitudinal axis of the balloon within the groove, upon inflation and deflation. The wires are flexible and are manufactured in such way that they are straight and sitting deeply in the folds of the balloon (14) when the balloon is deflated. Upon inflation, the balloon pushes the wires sitting in the grooves outside, bending the wires which negotiate the balloon surface.

Figure 16:
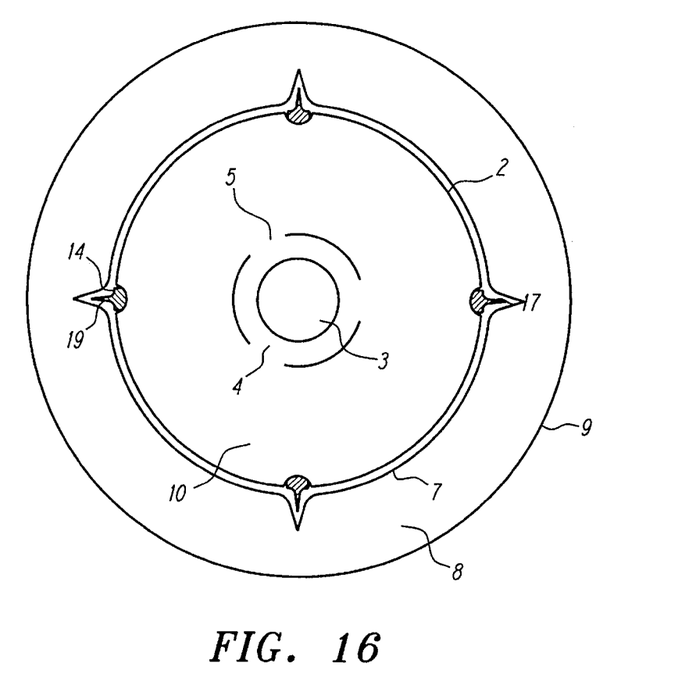
FIG. 16 is a cross-sectional view of the invention which includes shaped wires and the inflated balloon.

FIG. 16 shows a cross-section of the device and a normal vessel when the balloon is inflated. The balloon pushes the wires into the vessel wall making cuts (11) with sharp edges. Upon deflation of the balloon allows the wires to return into their original unbent position and submerging into the grooves and folds again.

Figure 22:
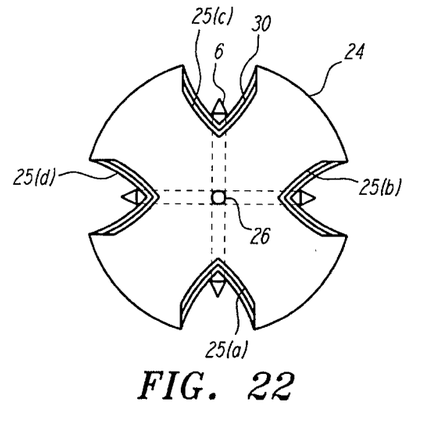
FIG. 22 is a cross-sectional view of a cutting balloon catheter with four radially arranged grooves.

FIG. 22 shows a cross section of an another preferred embodiment of a cutting balloon catheter, consisting of a catheter guidewire (24) with four radially arranged grooves at the distal end (25a–25d) and an inflatable balloon (30) sitting within the guidewire groove. In the shaft of the catheter guidewire is a system of lumens (26) which connect to the balloon and serve to allow inflation of the balloon such that the cutting edge (6) extends out beyond the catheter guidewire (24).

Figure 23:
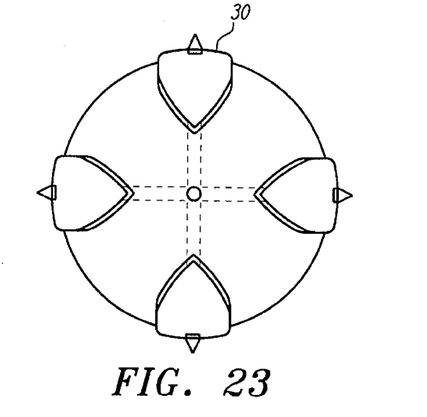
FIG. 23 is a cross-sectional view of an inflated cutting balloon catheter with four radially arranged grooves.

FIG. 23 shows the same cross section with the embodiment in the inflated stage.

Figure 24:
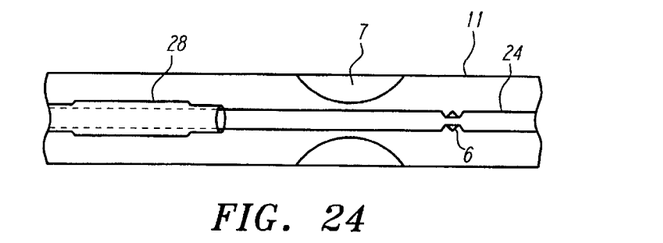
FIG. 24 is a side view of a pre-dilation conventional balloon catheter positioned over a guidewire with cutting edges.

FIG. 24 shows a side view of a variation on the preceding embodiment wherein a conventional balloon catheter (28) is positioned over the guidewire (24) proximal to the cutting edge (6) such that it can be advanced to dilate the previously cut vessel.

Various methods for dilating or recanalizing a vessel are also evident. In one method, a device is delivered with cutting edges to the vessel wall where dilation or recanalization is desired. The device is then actuated so that the cutting edges penetrate and make cuts into the vessel. A conventional balloon catheter is then moved into the previously cut vessel and inflated so as to dilate the vessel.

Figure 25:
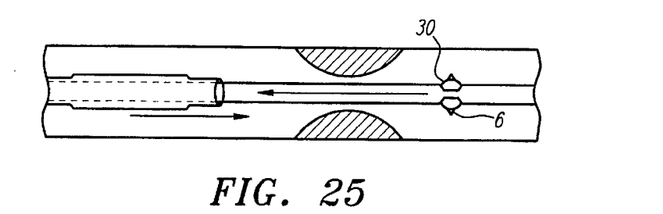
FIG. 25 demonstrates the step of moving a guidewire with actuated cutting edges through the vessel.
Figure 26:
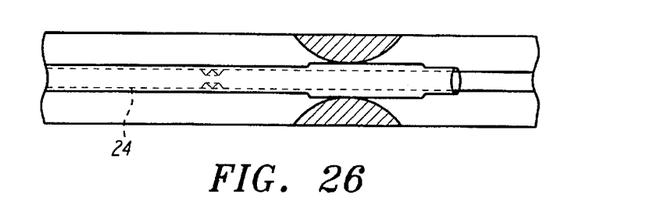
FIG. 26 demonstrates the step of moving the conventional balloon catheter into the previously cut vessel.
Figure 27:
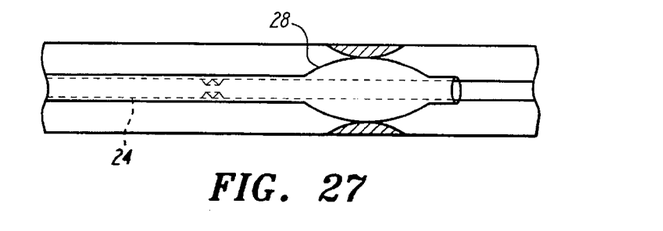
FIG. 27 demonstrates the seep of inflating the conventional balloon catheter to dilate the vessel.

In another method, a device such as disclosed in FIG. 24 is delivered distal to the vessel where dilation or recanalization is desired. FIG. 24. The device is then actuated and subsequently pulled back through the vessel so that the cutting edges make longitudinal cuts in the vessel wall. FIG. 25. A conventional balloon catheter is then moved into the previously cut vessel (FIG. 26) and inflated so as to dilate the vessel. FIG. 27. The foregoing methods may be also used to make longitudinal cuts in the vessel wall even when dilation or recanalization is not desired. Devices other than that of FIG. 24 as are known in the art may be used to perform these same generalized methods.

EXAMPLE

Experiment

Experimental animals included 18 farm pigs weighing from 42–61 kg, and 3 mongrel dogs weighing 28, 35 and 42 kg. The pigs were immobilized by delivering 15 mg/kg ketamine, 0.5 mg/kg acepromazine and 0.05 mg/kg atropine, all IM. For induction, 0.7 ml/g 2.5% thiopental IV was used both in pigs and dogs. The animals were then intubated and the anesthesia was maintained by 2–4% Enflurane. Eleven human cadaver arteries with different degrees of atherosclerotic disease from fibrotic to calcified plaques were also used.

The animals were fully heparinized during the procedure. The right carotid arteries were exposed and a 9F introducer sheath was inserted. The iliac and distal arteries were visualized by selective angiogram using non-ionizing contrast material from the iliac arteries after administration of 25 mg Lidocaine bolus in each iliac artery through a multipurpose catheter. The diameter of the vessels of different levels at 4× magnification was determined using the catheter tip and/or an external 3.5 mm reference point in order to choose a balloon size approximately 10% bigger than the vessel diameter.

Following intervention, the extent of the dilation necessary was determined by measuring the angiographic vessel and the balloon sizes and an average was calculated; 8–15% (average 12%) for the cutting balloon and 9–17% (14%) for the regular balloon. As a control, conventional angioplasty was performed on the right arteries in each animal using a conventional balloon catheter. The cutting balloon was used on the left artery of each animal.

For both the conventional and cutting balloon, the catheter was inserted without guiding or introducing catheters over an 0.018" steerable floppy guidewire. A balloon length from 20–45 mm was used. Dialations were started from the distal segments (1.7 mm diameter) and approached the proximal segments with the appropriate balloon size. Where the length of a given artery permitted, several dilations were made with the same balloon size 1 cm apart.

The conventional balloon catheters were inflated 3 times for 30 seconds each and the pressures in atmospheres needed to reach the nominal diameter of the balloon were registered. During initial experiments, repeated inflations of the cutting edge balloons induced slightly shifted cuts in the arterial wall so that in these experiments the cutting balloons were inflated only once for 30 seconds.

Angiograms were performed immediately after the dilation and at 1, 2 and 4 hours later, as well as at the time of sacrifice. In six cases angioscopy was also performed at the time of angioplasty and 2, 6, and 14 days later.

For histologic analysis the arteries were perfused through a canula placed right above the iliac bifurcation (and ligating the proximal aorta) by either 10% neutral buffered formalin or 2% cacodylated buffered glutaraldehyde under 100 mmHg pressure. The arteries were removed and postfixed, and embedded in either paraffin or Araldit. Cross sections were cut and stained.

Data Collection original angiographic vessel diameters, regular and cutting balloon diameters used at the given segment, pressure needed to obtain the nominal balloon diameter, number of inflations (i.e. 3 for the regular balloon and 1 for the cutting balloon), obtained diameter immediately after angioplasty and at 1, 2 and 4 hours following angioplasty as well as at the time of sacrifice were measured and recorded.

Angioscopic appearance, thrombus formation, and extravasation were noted. Acute histological changes such as endothelial denudation, platelet apposition, cellular changes, corkscrew nuclei, intimal tears and smooth muscle cell stretching were noted. Characterization of the cut made by the cutting at 2, 6 and 14 days after the procedure was recorded. The intimal proliferation as percentage of the original vascular area between the internal elastic lamina and adventitia was compared between the conventional balloon and the cutting balloon.

Results

Figure 17:
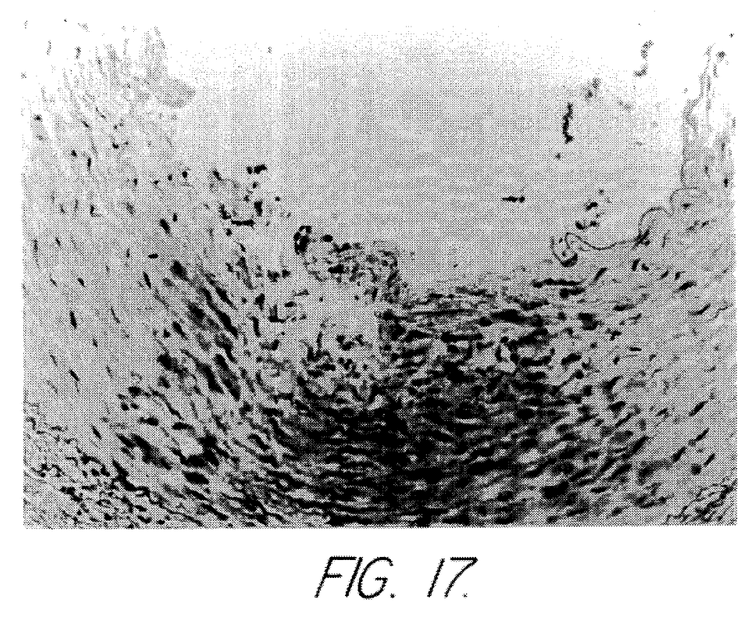
FIGS. 17–20 are photomicrography drawings.

1. Mistology:

Acute (n=7, 4 hours)
Conventional balloon:
FIG. 17 is a photomicrograph showing the acute histological changes that occurred after conventional balloon angioplasty. Incomplete endothelial denudation (i.e. the endothelium was preserved in certain areas), platelet aggregation, intimal tears often interrupting the intimal elastic lamina, smooth muscle cell stretching and corkscrew nuclei were observed.

Figure 18:
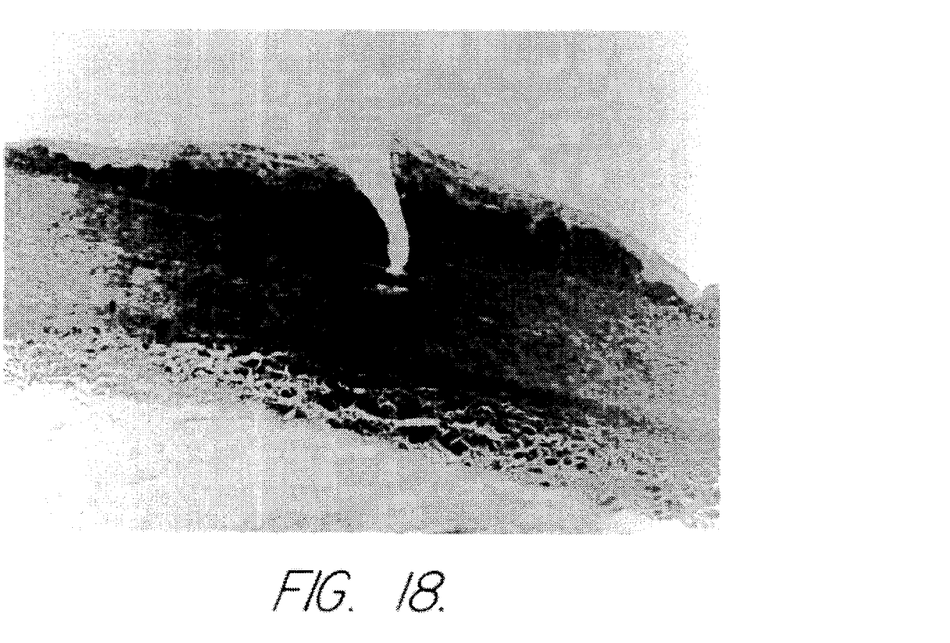

Cutting balloon:
FIG. 18 is a photomicrograph showing the acute histological changes that occurred after use of the cutting balloon. Cuts with sharp edges approximately ⅓ to ⅔ the depth of the medial layer, no intimal tears, intact internal elastic lamina except at the region of the cut and platelet apposition were observed.

Subacute (n=2, 6 days)
Conventional balloon:
An increase in the cellular activity around the lumen and proliferation of the intimal cells were observed.

Cutting balloon:
An intact luminal surface was observed and the site of the cut is filling up with granulation tissue and the surface covered by endothelium.

Figure 19:
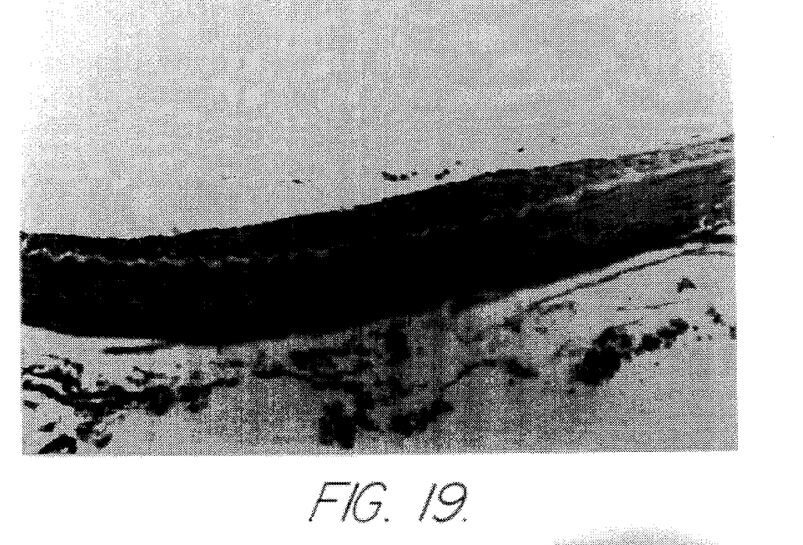

Longterm (n=10, 14 days)
Conventional balloon:
FIG. 19 is a photomicrograph showing the longterm histological affects of conventional balloon angioplasty. Intimal proliferation, proliferative areas in the media and a covering of endothelium on the surface was observed.

Figure 20:
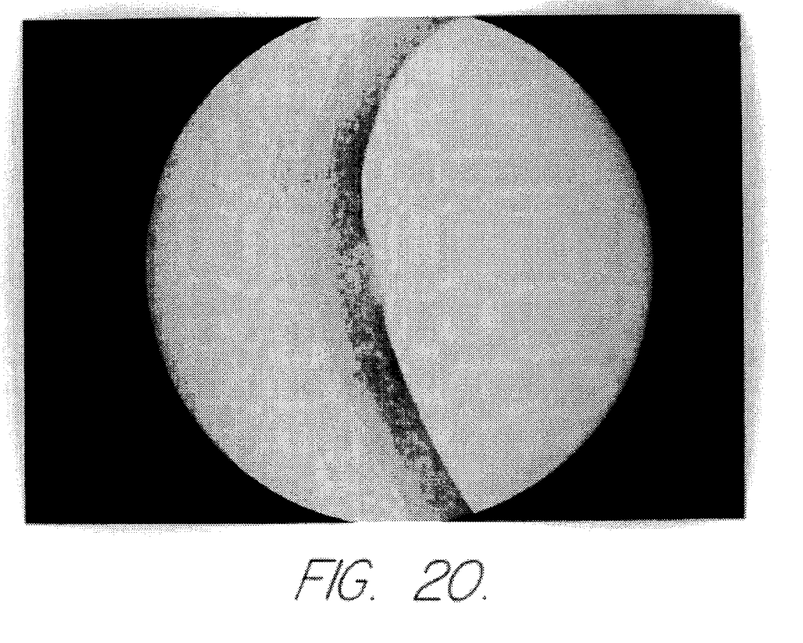

Cutting balloon:
FIG. 20 is a photomicrograph showing the longterm histological affects of the cutting balloon. The site of the cut is filled with granulation tissues and the edges of the cut (including the internal elastic (lamina) are slightly thrown up.

Figure 21:
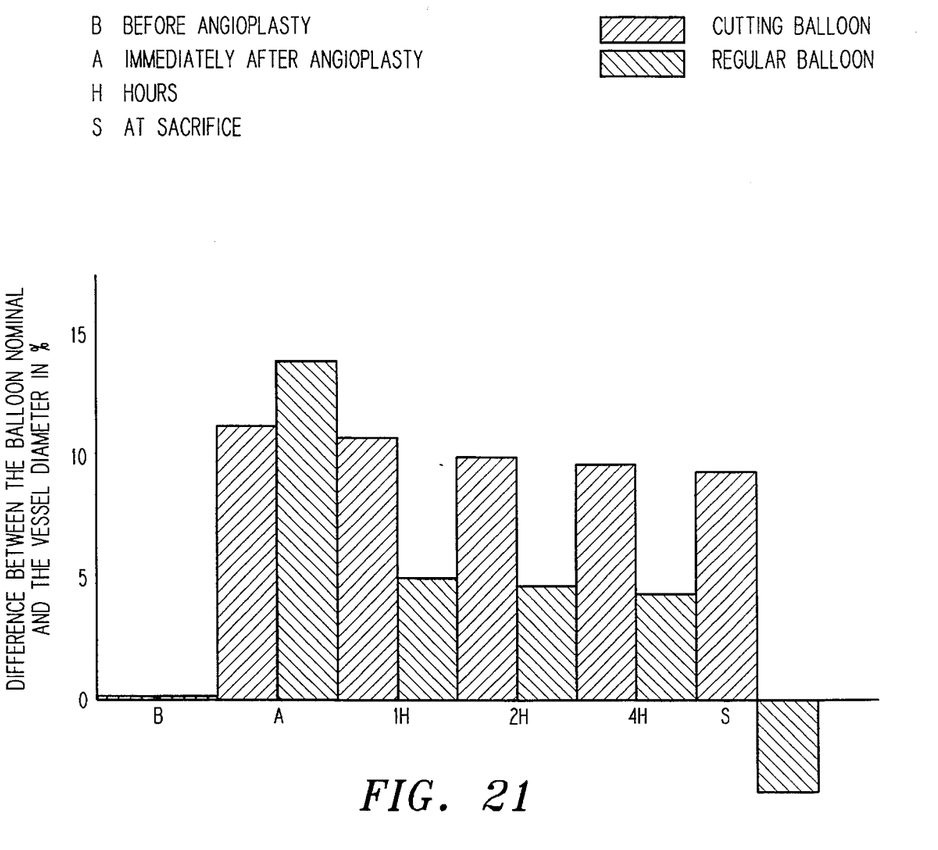
FIG. 21 is a chart which illustrates the difference between balloon nominal and vessel diameter.

2. Angiography:

The difference between the balloon nominal and the vessel diameter in percent before, immediately after and at various intervals after angioplasty, as well as at the time of sacrifice is shown in FIG. 21.

Angiographic measurement of the diameter of the arteries was increased immediately after dilation by both the conventional and cutting balloon. However, the diameter of the arteries after conventional balloon angioplasty decreased within one hour almost to the preprocedure diameter, while the arteries dilated by the cutting balloon catheter retained the increased diameter up to the time of sacrifice.

3. Balloon Pressures:

Pressure necessary to gain the nominal diameter of the balloon with the conventional balloon (3 inflation times) averaged approximately 6.8 atm, while the cutting balloon (1 inflation time) averaged 3.4 atm.

4. Intimal Hyperplasa:

With the conventional balloon there was a non-concentric intimal proliferation of 24% of the medial layer.

There was minimal subendothelial hyperplasia at the edges of the cuts with the cutting balloon.

It is to be understood that the above described embodiments are provided by way of example only, and not in a limiting sense. Other and further embodiments of the invention are readily apparent from the above description of the invention, and these embodiments are believed to be within the scope and spirit of the invention.

I claim:

1. A device for dilating or recanalizing a vessel comprising:

a catheter guidewire having a shaft, a proximal end and a distal end, and containing at least one groove at the distal end;

an inflatable balloon sitting within the guidewire groove;

a cutting edge mounted on the balloon and situated within the guidewire grove;

a system of lumens in the guidewire shaft connected to the balloon and serving to allow inflation of the balloon such that the cutting edge extends out beyond the guidewire and penetrates into the vessel wall; and a conventional balloon catheter positioned over the guidewire proximal to the cutting edge such that it can be advanced to dilate the previously cut vessel.

2. A device according to claim 1 wherein the guidewire contains four radially arranged grooves.

\* \* \* \* \*